United States Patent
Crotty et al.

(10) Patent No.: US 6,174,536 B1
(45) Date of Patent: *Jan. 16, 2001

(54) COSMETIC PRODUCT FOR REMOVAL OF KERATOTIC PLUGS FROM SKIN PORES

(75) Inventors: Brian Andrew Crotty, Branford; Philip Edward Miner, Newtown; Anthony Johnson, Fairfield; Alexander Paul Znaiden, Trumbull, all of CT (US)

(73) Assignee: Chesebrough-Pond's USA Co., division of Conopco, Inc., Greenwich, CT (US)

( * ) Notice: Under 35 U.S.C. 154(b), the term of this patent shall be extended for 0 days.

This patent is subject to a terminal disclaimer.

(21) Appl. No.: 09/236,163

(22) Filed: Jan. 22, 1999

Related U.S. Application Data

(62) Division of application No. 08/904,712, filed on Aug. 1, 1997, now Pat. No. 5,968,537.
(60) Provisional application No. 60/039,378, filed on Mar. 20, 1997.

(51) Int. Cl.$^7$ ........................................... A61K 7/48
(52) U.S. Cl. ..................... 424/402; 424/78.02; 424/401
(58) Field of Search ........................ 424/402, 78.02, 424/401

(56) References Cited

U.S. PATENT DOCUMENTS

| | | |
|---|---|---|
| 4,126,142 | 11/1978 | Saute . |
| 4,752,472 | 6/1988 | Kligman . |
| 4,762,124 | 8/1988 | Kerch et al. . |
| 4,990,339 | 2/1991 | Scholl et al. . |
| 5,026,552 | 6/1991 | Gueret et al. . |
| 5,254,338 | 10/1993 | Sakai et al. . |
| 5,466,456 | 11/1995 | Glover . |
| 5,512,277 | 4/1996 | Uemura et al. . |
| 5,605,694 | 2/1997 | Nadaud et al. . |
| 5,723,138 | 3/1998 | Bae et al. . |
| 5,736,128 | 4/1998 | Chaudhuri et al. . |
| 5,811,107 | 9/1998 | Gangadharan et al. . |
| 5,968,537 | * 10/1999 | Crotty et al. . |
| 5,993,838 | * 11/1999 | Crotty et al. . |

FOREIGN PATENT DOCUMENTS

| | | |
|---|---|---|
| 0 063 875 | 4/1982 | (EP) . |
| 0 309 309 | 3/1989 | (EP) . |
| 0 514 760 | 11/1992 | (EP) . |
| 2 144 133 | 2/1985 | (GB) . |
| 63-57508 | 12/1988 | (JP) . |

* cited by examiner

Primary Examiner—Raj Bawa
(74) Attorney, Agent, or Firm—Milton L. Honig

(57) ABSTRACT

A cosmetic product is provided for removing keratotic skin plugs. The product includes a flexible non-occlusive substrate sheet onto which a composition containing an anionic or nonionic polymer is deposited. The composition is treated to become dry non-tacky to the touch yet upon being wetted for use the composition again turns tacky and mobile. The method of application involves either directly moistening the product or indirectly moistening by first wetting a consumer's face in an area where the product is applied. Thereafter, water is allowed to evaporate leaving a film to which the keratotic plugs are bonded. The film is then peeled away concommittingly removing the plugs.

4 Claims, 1 Drawing Sheet

COSMETIC PRODUCT FOR REMOVAL OF KERATOTIC PLUGS FROM SKIN PORES

This Appln claims the benefit of U.S. Provisional No. 60/039,378 filed Mar. 20, 1997 and a divisional of Ser. No. 08/904,712 filed Aug. 1, 1997, which matured into U.S. Pat. No. 5,968,537, issued Oct. 19, 1997.

BACKGROUND OF THE INVENTION

1. Field of the Invention

The invention concerns a cosmetic product effective for the removal of keratotic plugs from skin pores.

2. The Related Art

Highly visual pores on facial skin surfaces are perceived, especially by women, to be a serious beauty problem. The conspicuous nature of this problem is caused by keratotic plugs formed within pores of the skin. Keratotic plugs are dead epidermal cells keratinized together with sebaceous matter and dirt. Absent proper treatment, not only will beauty suffer but also various dermatological problems may arise. Removal with detergents or with make-up removers (e.g. cold cream) have not provided adequate solution to the problem. Squeezing the skin in an attempt to remove keratotic plugs can lead to infections which can damage skin.

Peelable masks have been employed to attack plugged facial pores. They are applied as mobile films to the skin and peeled off after drying. Typically, the film is a nonionic polymer such as polyvinyl alcohol or Polyvinyl Pyrrolidone. Unfortunately, the mask approach is still not sufficiently effective for removing dirt from skin pores and especially for removing keratotic plugs.

Thus, there remains a need for a remover product which can effectively excise keratotic plugs formed in the pores of the skin and a method of removing keratotic plugs from the skin utilizing such remover products.

U.S. Pat. No. 5,512,277 (Uemura et al.) has reported a keratotic plug remover composition including use of a peelable mask formed from a resin functionalized with salt forming groups. Particularly preferred are cationic polymers which may be delivered as a poultice.

U.S. Pat. No. 4,126,142 (Saute) describes the use of sodium polystyrene sulfonate applied as a film to the face for cleansing skin and diminishing wrinkles. While apparently effective, further improvements in this technology are still necessary.

Accordingly, it is an object of the present invention to provide novel remover products which effectively remove keratotic plugs from skin pores.

It is another object to the present invention to provide new methods for effectively removing keratotic plugs from skin pores.

These and other objects will become more apparent from the summary and detailed description which follow.

SUMMARY OF THE INVENTION

A cosmetic product for removing keratotic plugs from skin pores is provided which includes:

(i) a flexible non-occlusive substrate sheet; and
(ii) a composition containing an anionic or nonionic polymer deposited onto the substrate sheet, the composition being dry non-tacky to the touch after deposition and upon being wetted for use the composition turns tacky and mobile.

BRIEF DESCRIPTION OF THE DRAWING

The invention will more fully be described by reference to FIG. 1 which is the sole drawing and illustrates a cross section of the cosmetic product.

DETAILED DESCRIPTION

Figure 1:
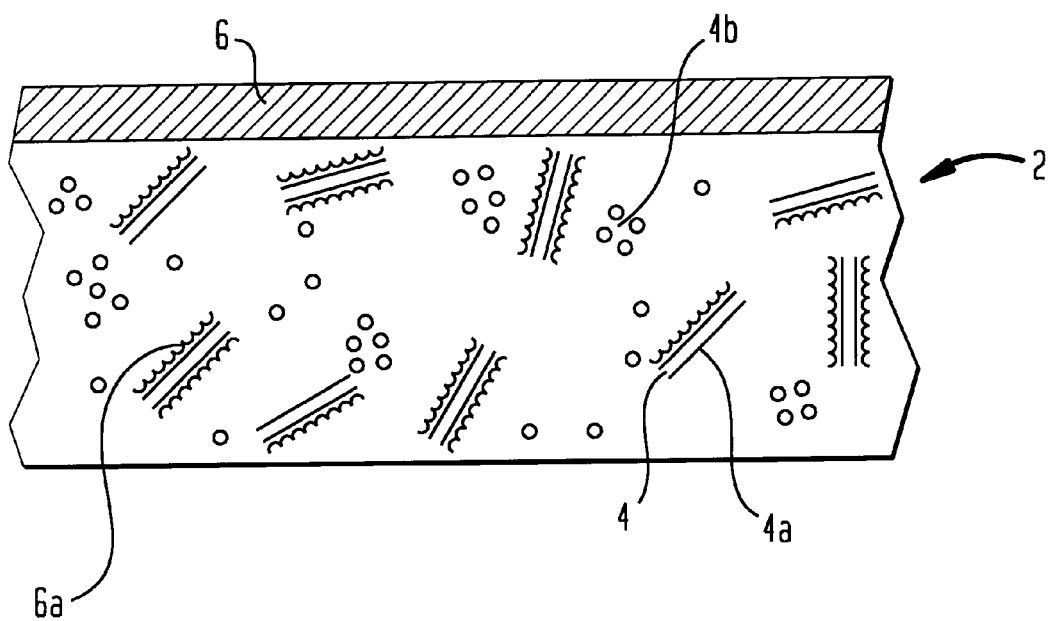

Now it has been discovered that keratotic plugs can be removed by applying to facial skin a cosmetic product in the form of a flexible non-occlusive substrate sheet impregnated with an adhesive composition containing an anionic or nonionic polymer. In a dry state, the composition is non-tacky to the touch. The product is used by either directly wetting the composition on the sheet or indirectly by wetting the face in areas to be contacted by the composition. In either instance, the wetting agent interacts with the composition so it becomes tacky and sufficiently mobile to flow into skin pores. Pure water is the preferred wetting agent. However, other fluid systems or gels could be employed. Suitable fluids would include alcohols such as ethanol, propanol, propylene glycol, polyethylene glycol, polypropylene glycol and especially mixtures of these alcohols with water. Gels would normally consist of fluid (particularly water) and structuring agents such as Carbomer.

Subsequent to wetting the composition is allowed to dry over the area of treatment. During drying the keratotic plugs stickingly adhere to the composition. Advantageously the drying period ranges from 1 minute to 5 hours, preferably from 5 minutes to 1 hour, optimally from 10 to 20 minutes. Thereafter, the dried composition with adhered plugs is peeled from the skin.

Mobility of the composition may be measured by yield point. The yield point should range from 1 to 400 Pascals, preferably from 20 to 200, optimally from 50 to 100 Pascals.

The composition will include a polymer which may either be anionic, nonionic or mixtures thereof. Further, there may be utilized combinations of different anionic or nonionic polymers. Examples of nonionic polymers suitable for film deposition are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1.1) wherein such copolymers are 50% esterified with a saturated alcohol containing from 1 to 4 carbon atoms such as ethanol or butanol; and acrylic copolymers, terpolymers, etc., containing acrylic acid or methacrylic acid esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerized terpolymer of methacrylic acid, n-butyl acrylate and ethyl acrylate (e.g., in a weight percent ratio of 31:42:27, respectively).

Further examples of nonionic film forming polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 under the trademark PVP K-90 and those having an average molecular weight of about 1,000,000 sold under the trademark of PVP K-120. Particularly preferred is poly(methyl vinyl ether/maleic anhydride) as an unneutralized resin available from ISP Corporation under the trademark Gantrez® S-97 BF.

Anionic film forming polymers often are derived from the nonionic types which include carboxylic acid functions. Alkaline agents are employed to neutralize the carboxylic acid or anhydride transforming them into anionic salts. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Most preferred is AMP.

Particularly preferred anionic polymers are the salts of poly(methyl vinyl ether/maleic anhydride) and polystyrene sulfonic acid. The former is obtained by at least partial neutralization of Gantrez® S-97 BF and the latter available from the National Starch & Chemical Company under the trademarks Versa TL-501 and Flexan® 130 having respective molecular weights of about 500,000 and 100,000. Other polymer films which may be employed and are commercially available are listed in the Table below.

| POLYMER TRADEMARKS (SUPPLIER) | CTFA DESIGNATIONS |
|---|---|
| Resyn ® 28-1310 (NSC) | Vinyl acetate/crotonic acid copolymer |
| Resyn ® 28-2930 (NSC) | Vinyl acetate/crotonic acid/vinyl neodecanoate copolymer |
| Resyn ® 28-2913 (NSC) | Vinyl acetate/crotonic acid/vinyl neodecanoate copolymer |
| Versatyl ® 40 (NSC) | Octylacrylamide/acrylates copolymer |
| Versatyl ® 42 (NSC) | Octylacrylamide/acrylates copolymer |
| Experimental Resin (NSC) | Vinyl acetate/vinyl neodecanoate/maleic half-ester |
| Ultrahold-8 ® (BASF) | Acrylate/acrylamide copolymer |
| Luviset ® CAP (BASF) | Vinyl acetate/crotonic acid/vinyl propionate copolymer |
| PVP K-30 (ISP) | PVP |
| PVP/VA E-335 (ISP) | PVP/Vinyl acetate copolymer |
| PVP/VA E-735 (ISP) | PVP/Vinyl acetate copolymer |
| Gantrez ® ES-225 (ISP) | Ethyl ester of PVM/MA copolymer |
| Gantrez ® ES-425 (ISP) | Butyl ester of PVM/MA copolymer |
| Gaffix ® VC-713 (ISP) | Vinyl caprolactam/PVP/dimethyl aminoethyl methacrylate copolymer |

Most polymers suitable for the present invention will be relatively brittle when dried. Therefore, they require a supporting surface which is a flexible substrate sheet. Substrate sheets of the present invention must be non-occlusive to allow water evaporation from the deposited polymer as the film maturates. Non-occlusivity or breathability is achieved either through use of a hydrophobic substrate having physical porosity (e.g. pore channels) or a hydrophilic substrate wherein the material of construction inherently allows for breathability. Suitable materials include cellulosics such as rayon, wool, cotton, linen and combinations thereof. They may be woven or nonwoven. Nonwoven rayon is a preferred substrate. Ordinarily hydrophobic substrates are unsuitable. For instance, untreated polyethylene is hydrophilic but hydrophilically treated (e.g. coated) polyethylene may be useful. However, if hydrophobic substances are so constructed with a fiber geometry to allow for breathability, they may also be employed. Under these conditions, polyesters, polyamides, vinyl resins and other thermoplastic fibers could be suitable. Materials formed from combinations of cellulosic with thermoplastic fibers may also be employed subject to breathability. For instance, a hydrophilic polypropylene/rayon combination can be employed for the present invention.

It is important to employ a ratio of composition to substrate in amount ranging from 0.1:1 to 1,000:1, preferably 0.5:1 to 100:1 and optimally 0.8:1 to 10:1 by weight. The polymer ordinarily will constitute from 50 to 100%, preferably from 75 to 99%, optimally from 85 to 95% by weight of the composition deposited onto the substrate sheet.

FIG. 1 provides a cross section of a tape typical of the present invention. The tape is formed of a flexible non-woven rayon substrate sheet 2. Random fibers 4 are shown laying longitudinally 4a or cut 4b by the cross section. On one surface of the substrate sheet is deposited a composition formed essentially of a polymer 6 which at least partially impregnates the surface. Impregnated polymer 6a is seen as a coating on internal fibers. When wetted, composition 6 turns tacky and can flow into skin pores to adhesively contact keratotic plugs.

Certain additives may be included along with the deposited polymer. Most useful may be a surfactant which can be selected from anionic, cationic, nonionic or amphoteric actives. Illustrative nonionic surfactants are alkoxylated compounds based on $C_{10}$–$C_{22}$ fatty alcohols and acids, and sorbitan. These materials are available, for instance, from the Shell Chemical Company under the Neodol trademark. Copolymers of polyoxypropylene-polyoxyethylene, sold by the BASF Corporation under the Pluronic trademark, are sometimes also useful. Alkyl polyglycosides available from the Henkel Corporation or alkyl glucamides may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates and sodium fatty acyl isethionate.

Amphoteric surfactants include such materials as dialkylamine oxide and various types of betaines (such as cocoamidopropyl betaine).

The surfactant when present may range from 0.01 to 10% by weight of the total composition deposited onto the sheet.

Minor adjunct ingredients may also be included such as fragrances, skin care additives, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A non-woven resin bonded 100% rayon white non-apertured fabric from Vertec was employed as a flexible substrate. Flexan® 130 (sodium salt of sulfonated polystyrene as a 30% polymer in aqueous solution) was deposited onto the rayon fabric.

The fabric for each test strip was a small disk accurately weighed. These disks were submerged in the polymer adhesive solution for about 5 seconds. Thereafter they were dried. Higher loadings were obtained by repeated multiple submergence. To achieve lower loading levels, the 30% aqueous solution was diluted downward to a level of 15% solids and 7.5% solids. These diluted solutions were then used for receiving fabric which was submerged therein.

An area of a panelist's face was chosen which contained several plugged pores. These plugged pores were then counted. Water was applied to the area and the adhesive patch was placed over it. Next, the patch was allowed to dry and then it was peeled off. The number of removed plugs were counted on the adhesive patch. The percent plugs removed was calculated to reflect adhesive patch efficiency. From these values maximum and minimum loading levels were determined.

$$\% \text{ Loading} = \frac{(\text{Wt. of rayon with adhesive} - \text{Wt. of dry rayon})}{(\text{Wt. of dry rayon})} \times 100$$

$$\% \text{ Plugs Pulled} = \frac{\# \text{ of plugs pulled}}{\# \text{ of plugged pores}} \times 100$$

TABLE I

RESULTS

| % Dried Flexan 130 Loaded on Rayon | % Plugs Pulled |
|---|---|
| 120 | 0 |
| 164 | 90–100 |
| 485 | 90–100 |
| 1100 | 80 |
| 2132 | 70 |
| 3369 | 10 |
| 3815 | 10 |
| 6451 | 10 |

The experiments reported in Table I reveal that there is an optimum loading range for a given adhesive polymer or formulation on a given fabric. It is to be noted that different polymers with different drying rates and even different fabrics may strongly influence plug removal levels.

EXAMPLE 2

A variety of polymers were evaluated for their adhesive effects in removing keratotic plugs from the skin. The polymers listed in Table II below were coated onto a non-woven resin bonded rayon (1 ounce/square yard). A knife-over-roll was utilized in the coating operation. After coating, the non-woven polymer impregnated substrate sheets were dried at 75° C. in a convection oven. They were then cut into small patches.

Similar to the test procedure described under Example 1, the test patches were applied to the face of panelists in an area containing several plugged pores. The plugged pores were counted. Water was applied to the patch and it was then placed over the test area with wet side down. Next, the patch was allowed to dry whereupon it was peeled off. The number of plugs removed were counted as they appeared on the adhesive patch. Percentage of plugs removed were calculated to reflect efficiency of the test product.

TABLE II

| POLYMER | % DRIED POLYMER ON NON-WOVEN | % PLUGS REMOVED |
|---|---|---|
| Dextrine | 409 | 5–15 |
| Polyvinyl Alcohol | 441 | 10–20 |
| Polyvinyl Acetate | 347 | 30–40 |
| Polyacrylamidomethylpropane Sulfonic Acid | 119 | 5–15 |

TABLE II-continued

| POLYMER | % DRIED POLYMER ON NON-WOVEN | % PLUGS REMOVED |
|---|---|---|
| Polyacrylamidomethylpropane Sulfonic Acid | 275 | 25 |
| Poly(methyl vinyl ether/maleic anhydride) | 113 | 90–100 |
| 98% Poly(methyl vinyl ether/maleic anhydride) + 2% 2-amino-2-methyl-1-propanol | 116 | 80–95 |
| 90% Poly(methyl vinyl ether/maleic anhydride) 10% Polyacrylamido-methylpropane Sulfonic Acid | 145 | 90–100 |

EXAMPLE 3

Poly(Methyl Vinyl Ether Maleic Anhydride) Gantrez S-97 BF was coated by knife-over-roll (25 mil.) over various nonwoven materials. After coating, the nonwoven materials were dried at 75° C. in a convection oven and then cut into small patches. The test procedure was similar to that reported under Example 2. Results are reported in Table III.

TABLE III

| NONWOVEN | % PLUGS PULLED | OBSERVATIONS |
|---|---|---|
| PGI 5255 Rayon Resin bonded (1 oz./sq. yard) | 90–100 | Nice appearance |
| Veratec 9408810 Polyester/cellulose Wet laid (1.2 oz/sq. yard) | 70–100 | Nice appearance: Nonwoven may be too weak |
| Veratec 2006094 Polypropylene Thermal Bond (.6 oz/sq. yard) | 40–60 | Nice appearance |
| Veratec Polyethylene (.5 oz/sq. yard) | 10 | Poor appearance: When used in application adhesive dried very slow. |

The foregoing description and Examples illustrate select embodiments of the present invention. In light thereof, various modifications would be suggested to one skilled in the art all of which are within the purview and spirit of this invention.

What is claimed is:

1. A method for removing keratotic plugs from skin pores on an area of the nose consisting essentially of:
   (a) wetting an area of skin to be treated with a wetting agent comprising a fluid;
   (b) applying a plug removing product onto the area, the product comprising:
      (i) a flexible non-occlusive substrate sheet wherein the sheet is selected from the group consisting of rayon, polyester, polypropylene and mixtures thereof; and
      (ii) a composition containing an anionic or nonionic water-soluble polymer deposited onto the substrate sheet, the composition being dry non-tacky to the touch after deposition and upon being wetted for use the composition turns tacky and mobile;
   (c) allowing the fluid to tackify the composition and then to evaporate from the area covered by the product; and
   (d) peeling away the product from the skin thereby removing keratotic plugs now adhesively attached to the composition.

2. The method according to claim 1 wherein the fluid is selected from the group consisting of water, alcohol and mixtures thereof.

3. A method for removing keratotic plugs from skin pores from an area of the nose through use of a cosmetic product, the product comprising:
  (i) a flexible non-occlusive substrate sheet wherein the sheet is selected from the group consisting of rayon, polyester, polypropylene and mixtures thereof; and
  (ii) a composition containing an anionic or nonionic water-soluble polymer deposited onto the substrate sheet, the composition being dry non-tacky to the touch after deposition and upon being wetted for use the composition turns tacky and mobile;
  the method consisting essentially of:
  (a) placing a wetting agent comprising a fluid onto a surface of the cosmetic product whereon the composition is deposited thereby turning the composition into a tacky and mobile material;
  (b) applying the wetted cosmetic product onto an area of skin to be treated;
  (c) allowing fluid to evaporate from the area covered by the product; and
  (d) peeling away the product from the skin on the nose thereby removing keratotic plugs now adhesively attached to the composition.

4. The method according to claim 3 wherein the fluid is selected from the group consisting of water, alcohol and mixtures thereof.

* * * * *